US011291700B2

(12) United States Patent
Kane et al.

(10) Patent No.: US 11,291,700 B2
(45) Date of Patent: Apr. 5, 2022

(54) WATER-SOLUBLE CANNABINOIDS AND METHODS OF MAKING SAME

(71) Applicant: Nature's Delivery System, LLC, West Chester, PA (US)

(72) Inventors: James F. Kane, West Chester, PA (US); Keith Butler, Rixeyville, VA (US)

(73) Assignee: Nature's Delivery System, LLC, West Chester, PA (US)

( * ) Notice: Subject to any disclaimer, the term of this patent is extended or adjusted under 35 U.S.C. 154(b) by 125 days.

(21) Appl. No.: 16/210,267

(22) Filed: Dec. 5, 2018

(65) Prior Publication Data

US 2019/0167740 A1 Jun. 6, 2019

Related U.S. Application Data

(60) Provisional application No. 62/594,662, filed on Dec. 5, 2017.

(51) Int. Cl.
| | |
|---|---|
| *A61K 35/00* | (2006.01) |
| *A61K 36/00* | (2006.01) |
| *A61K 36/185* | (2006.01) |
| *A61K 9/14* | (2006.01) |
| *A61K 31/05* | (2006.01) |
| *A61K 9/107* | (2006.01) |
| *A61K 47/46* | (2006.01) |

(52) U.S. Cl.
CPC ............ *A61K 36/185* (2013.01); *A61K 9/107* (2013.01); *A61K 9/14* (2013.01); *A61K 31/05* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 7,687,074 | B2 | 3/2010 | Folan et al. |
| 10,028,987 | B1 | 7/2018 | Pillsbury |
| 2007/0270377 | A1 | 11/2007 | Kawakami et al. |
| 2015/0216902 | A1 | 8/2015 | Fardoussi |
| 2017/0020945 | A1* | 1/2017 | Reillo .................... A23L 29/035 |
| 2018/0117161 | A1* | 5/2018 | Docherty ................ A61P 25/16 |

OTHER PUBLICATIONS

Lopez et al. ("Human milk fat globules: Polar lipid composition and in situ structural investigations revealing the heterogeneous distribution of proteins and the lateral segregation of sphingomyelin in the biological membrane", Colloids and Surfaces B: Biointerfaces 83 (2011) 29-41) (Year: 2011).*
Lipophilic Microconstiutents of Milk (see website article (Abstract), http://link.springer.com/chapter/10.1007/978-0-387-74087-4_3, pp. 1-21, copyright information 2008) (Year: 2008).*
Bezelgues et al. ("Short communication; Milk fat globule membrane as a potential delivery system for liposoluble nutrients", Journal of Diary Science vol. 92 No. 6, 2009, pp. 2524-2528) and Lipophilic Microconstiutents of Milk (see website article (Abstract) (Year: 2009).*
Khan et al., "Advanced drug delivery to the lymphatic system: lipid-based nanoformulations," International Journal of Nanomedicine, 2013, 8: pp. 2733-2744.
Argov et al., "Milk Fat Globule Structure & Function; nanoscience comes to milk production," Trends Food Science & Technology, 19(12), 2008, pp. 1-13.
Black, "Development and Physiological Regulation of Intestinal Lipid Absorption. I. Development of intestinal lipid absorption: cellular events in chylomicron assembly and secretion," AJP-Gastrointest Liver Physiol, vol. 293,2007, pp. G519-G524.
Cano-Ruiz et al., "Effect of Homogenization Pressure on the Milk Fat Globule Membrane Proteins," Journal of Dairy Science, vol. 80, 1997, pp. 2732-2739.
Dewettinck et al., "Nutritional and technological aspects of milk fat globule membrane material," International Dairy Journal, vol. 18, issue 5, 2008, pp. 436-457.
Kailasapathy, "Chemical Composition, Physical, and Functional Properties of Milk and Milk Ingredients," Dairy Processing and Quality Assurance, 2nd edition, 2016, pp. 77-105.
Lopez et al., "Lipid droplets coated with milk fat globule membrane fragments: Microstructure and functional properties as a function of pH," Food Research International, 91, 2017, pp. 26-37.
Michalski et al., "The supramolecular structure of milk fat influences plasma triacylglycerols and fatty acid profile in the rat," European Journal of Nutrition, vol. 45, 2016, pp. 215-224.
Rosqvist et al., "Potential role of milk fat globule membrane in modulating plasma lipoproteins, gene expression, and cholesterol metabolism in humans: a randomized study," The American Journal of Clinical Nutrition, v. 102, 2015, pp. 1-77.
Smoczyński et al., "Composition and Structure of the Bovine Milk Fat Globule Membrane—Some Nutritional and Technological Implications," Food Reviews International, 2012, 28: pp. 188-202.
Thompson, "Absorption of fat-soluble vitamins and sterols," J clin Path., 24, Suppl. (Roy. Coll. Path.), 5: pp. 85-89.
Mohan, "Casein Micelles and their Properties: Polydispersity Association with Vitamin A and Effect of Ultra-High Pressure Homogenization," University of Tennessee—Knoxville, 2014.
Wang et al., "In Search of Preventative Strategies: Novel Anti-Inflammatory High-CBD Cannabis Sativa Extracts Modulate ACE2 Expression in COVID-19 Gateway Tissues," doi:10.20944/preprints202004.0315.v1, posted Apr. 19, 2020, 12 pages.
Wölfel, et al. "Virological assessment of hospitalized patients with COVID-2019," Nature Research, vol. 581, May 28, 2020, pp. 465-469 with appendices (12 pages).

(Continued)

*Primary Examiner* — Michael Barker
*Assistant Examiner* — Randall O Winston
(74) *Attorney, Agent, or Firm* — Kilyk & Bowersox, P.L.L.C.

(57) ABSTRACT

A process is provided for improving the water solubility of cannabinoids by combining cannabinoids with fat globules obtained from animals, plants, or synthetic chemistry. The animals can be mammals or non-mammals. The plants can be whole plants, tissue cultures, or genetically engineered plants. The fat globules can be used in their natural environment, and/or following processing, and/or as separated or purified particles.

22 Claims, 5 Drawing Sheets

(56) References Cited

OTHER PUBLICATIONS

Office Action for U.S. Appl. No. 16/898,804, issued by the U.S. Patent and Trademark Office, dated Aug. 7, 2020, including Form 892, 8 pages.

* cited by examiner

WATER-SOLUBLE CANNABINOIDS AND METHODS OF MAKING SAME

CROSS-REFERENCE TO RELATED APPLICATION

The present application claims priority to U.S. Provisional Patent Application No. 62/594,662, filed Dec. 5, 2017, which is incorporated herein in its entirety by reference.

FIELD OF THE INVENTION

The present invention relates to methods and compositions that provide water-soluble forms of cannabinoid molecules.

BACKGROUND OF THE INVENTION

Cannabis has been used medicinally for thousands of years. The chemical compounds found in the Cannabis plant are called cannabinoids. There are over 80 different cannabinoids in marijuana. Most health benefits of marijuana are associated with the cannabidiol (CBD) cannabinoid. Among the many medicinal uses of CBD, be used as an analgesic, an anti-inflammatory, an appetite stimulant, an anti-psychotic, an anti-epileptic, an anti-spasmodic, an anti-diabetic and an anti-psoriatic.

Marijuana plant products that contain CBD include hemp oil and hemp oil extracts. Hemp oil is not water-soluble and typically is known to have an unpleasant taste. A need exists for an ingestible form of hemp oil and hemp oil extracts that have a more tolerable taste. A need also exists for water-soluble forms of hemp oil and hemp oil extracts that can be mixed or added to a wide variety of food stuffs and drinks so as to be better ingestible and better digestible.

SUMMARY OF THE INVENTION

The present invention provides a method of improving the water-solubility and bioavailability of cannabinoid molecules. Fat globules can be used for such purpose. Fat globules from milk, for example, with or without associated membranes (MFGM), contain an interior that is highly water-insoluble and is, therefore, a "landing place" for other lipophilic substances such as the cannabinoids and oils extracted from Hemp and/or Cannabis.

The fat globules, which can be derived from a variety of sources, such as animals, plants, plant cell cultures, or fermentation processes, can be used as carriers of cannabinoids as well as Hemp and/or Cannabis oil extracts. The fat globules facilitate the creation of a composition that provides a greatly improved solubility for the lipophilic cannabinoids and oil extracts. By using "natural fat globules," which the intestinal tract of humans can handle and metabolize, the bioavailability of the cannabinoids and oils can be greatly enhanced.

DETAILED DESCRIPTION OF THE INVENTION

Figure 1:
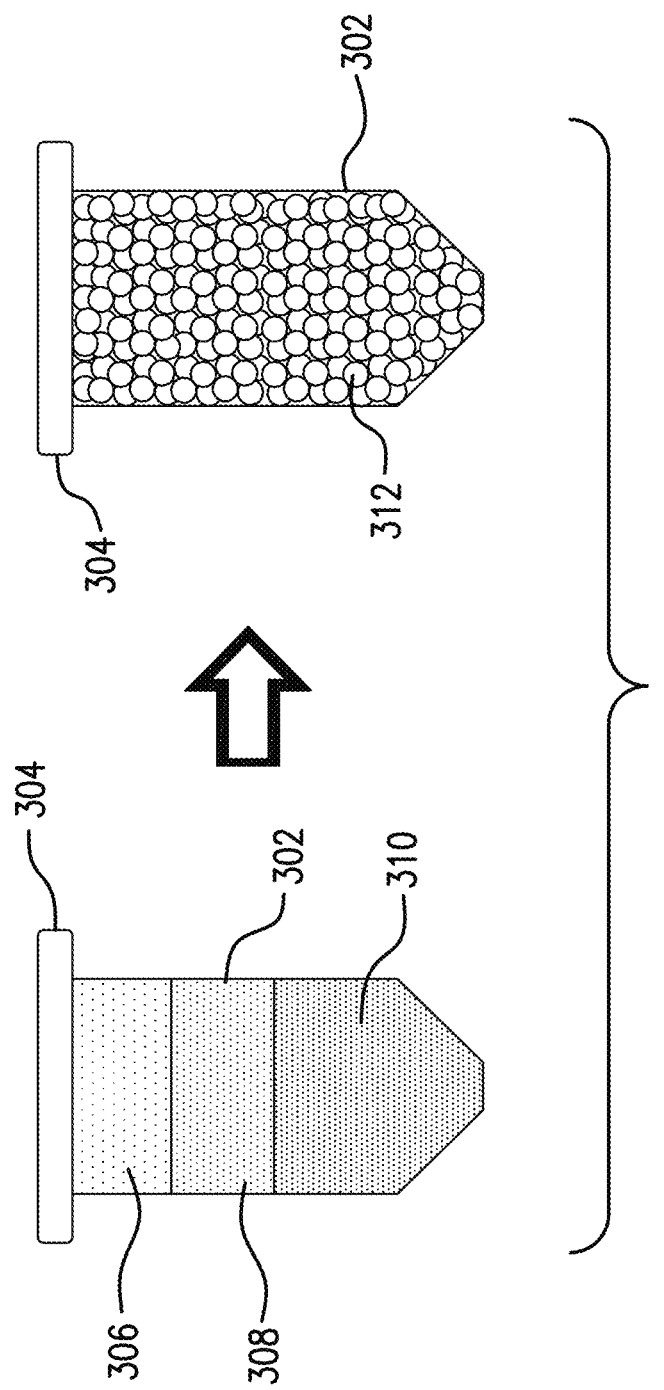
FIG. 1 is a schematic diagram of a method involving mixing a three-part mix of milk fat globules, hemp oil, and water, to form an emulsion according to various embodiments of the present invention.

According to various embodiments of the present invention, a soluble form of a cannabinoid, hemp oil, cannabis oil, or a combination thereof, is provided. The soluble form comprises, in combination, (a) a cannabinoid, hemp oil, cannabis oil or combination thereof, and (b) fat globules from a mammalian source, animal source, plant source, synthetic source, or a combination thereof. Components (a) and (b) can be mixed together to form a mixture, solution, emulsion, suspension, powder, paste, or other composition providing a soluble form of a cannabinoid, hemp oil, cannabis oil, or a combination thereof. The source of fat globules can comprise raw milk, a processed product of raw milk, or the like. The source of fat globules can comprise a plant. The source of fat globules can be a chemically synthesized source. The source of fat globules can comprise an animal other than a mammal. The fat globules can be in a powdered form, liquid form, or both.

The cannabinoid, hemp oil, cannabis oil, or combination thereof, can comprise naturally occurring molecules that are purified from hemp, cannabis, or another plant source. The cannabinoid, hemp oil, cannabis oil, or combination thereof can be synthetically prepared. The cannabinoid, hemp oil, cannabis oil, or combination thereof can be derived from genetically engineered microorganisms grown in a controlled environment. The cannabinoid, hemp oil, cannabis oil, or combination thereof can be derived from a genetically engineered plant that is grown either in a field or in a greenhouse. The cannabinoid, hemp oil, cannabis oil, or combination thereof can be derived from plant cell cultures. The cannabinoid, hemp oil, cannabis oil, or combination thereof can comprise hemp oil, cannabis oil, and cannabinoids homogenized together, for example, before the hemp oil, cannabis oil, and cannabinoids are mixed together with fat globules.

The present invention also provides a method of forming a soluble form of a cannabinoid, hemp oil, cannabis oil, or a combination thereof. The method can comprise mixing together components (a) and (b) to effect migration of component (a) into component (b), wherein component (a) comprises a cannabinoid, hemp oil, cannabis oil or combination thereof, and component (b) comprises fat globules from a mammalian source, animal source, plant source, synthetic source, or a combination thereof. The mixing can comprise stirring together at a rate of from about 5 rpm to about 12,000 rpm, for example, from about 5 rpm to about 5000 rpm, from about 10 rpm to about 1000 rpm, from about 50 rpm to about 800 rpm, or from about 100 rpm to about 500 rpm. The stirring can comprise mixing components (a) and (b) together to form a mixture and subjecting the mixture to centrifugation to effect migration of component (a) into component (b). The mixing can comprise mixing components (a) and (b) together to form a mixture and subjecting the mixture to sonication, homogenization, centrifugation, or the like, to effect migration of component (a) into component (b).

According to various embodiments of the present invention, component (b) can comprise a powder and component (a) can be mixed directly with the powder.

Component (a) and component (b) can be mixed together at a respective weight ratio of from 1:0.1 to 1:100, for example, from 1:0.5 to 1:50, from 1:1 to 1:20, from 1:1 to 1:10, from 1:2 to 1:8, or from 1:2 to 1:5, for a component (b) that comprises 100% by weight fat globules. Diluents, for example, water, deionized water, fruit juice, or the like, can also be added in amounts of from about 5% by weight or more, based on the total weight of components (a) and (b) combined. Diluents can be added in amounts of from about 10% by weight or more, 20% by weight or more, 30% by weight or more, 40% by weight or more, 50% by weight or more, from 10% by weight to 95% by weight, from 20% by weight to 90% by weight, from 30% by weight to 85% by weight, or from 40% by weight to 80% by weight, based on the total weight of components (a) and (b) combined.

When component (b) comprises a source of milk fat globules, component (a) and component (b) can be mixed together at a respective weight ratio of from 1:0.1 to 1:100, for example, from 1:0.5 to 1:50, from 1:1 to 1:20, from 1:1 to 1:10, from 1:2 to 1:8, or from 1:2 to 1:5, for a source containing from 1% by weight to 100% by weight milk fat, for example, from 2% by weight to 75% by weight milk fat, from 4% by weight to 66% by weight milk fat, from 10% by weight to 40% by weight milk fat or from 12% by weight to 38% by weight milk fat.

In various embodiments of the present invention, milk and milk products can be used as a source of fat globules. Milk is an emulsion comprising fat particles (globules) dispersed in an aqueous (watery) environment. The fat globules do not coalesce and form a separate layer (oil off or churn) because they are protected by a membrane layer that keeps the fat particles separated from the water phase. The principal group of milk proteins, the caseins, are not soluble in water and exist in milk as smaller particles (<300 nm) called micelles.

Herein, milk is defined as a dispersion of milk fat globules (fat particles) and casein micelles (protein particles) dispersed in a continuous phase of water, sugar (lactose), whey proteins, and minerals.

Milk Plasma is defined herein as what is left after fat globules are separated out of milk; which is equivalent to skim milk for practical purposes.

Milk Serum is defined herein as what is left after both fat globules and casein micelles are taken away from milk; which is equivalent to cheese whey for most practical purposes.

Milk permeate is defined herein as what is left after fat globules, casein micelles, and whey proteins are taken away from milk.

The fat emulsion layer containing the milk fat globules (MFG) can be used according to embodiments of the present invention. Different structures are formed by the diverse nature of the fat globules. Molecules of interest can be added to these diverse structures. The milk fat globules can be used as such or first be made more uniform by homogenization. Molecules of interest can be added with or without homogenization of the fat globules, and before, during, or after homogenization.

Upon ingestion, the milk fat globules can make it to the small intestine where they are degraded and adsorbed into the blood. Such digestion is described, for example, in *Milk Fat Globule structure & function; nanoscience comes to milk production*, Nurit Argova, Danielle G. Lemaya, and J. Bruce Germana, *Trends Food Sci Technol.* 2008 December; 19 (12): doi:10.1016/j.tifs.2008.07.006, which is incorporated herein in its entirety by reference.

Fat-soluble vitamins are contained within fat globules. These fat globules are already designed to deliver fat-soluble materials, i.e., water-insoluble materials, to the blood stream. According to various embodiments of the present invention, water-insoluble materials such as cannabinoids and hemp oils can be combined with milk fat globules to provide or increase water solubility of such materials, so such materials can be better delivered to the blood stream.

It has been found that fat is absorbed about three-fold more effectively when it is presented in the intestinal tract as a micelle rather than an emulsion. Through evolution, mammals have developed an efficient means to deliver fat soluble materials to their blood stream via a fat globule. These MFG consist of a lipid core surrounded by a monolayer of polar lipids and proteins. The MFG do not coalesce and form a separate layer (oil off or churn) because they are protected by a membrane monolayer layer that keeps the fat particles separate from the water phase. When first produced, the MFG are surrounded by the lipid bilayer membrane of the secretory cell, containing all of the components normally found in this membrane. These MFG with an associated cell membrane, designated MFGM, are present in a heterogeneous array of sizes. As the most complex entity in milk, the MFG are the macrostructure most affected by processing and homogenization, during which, the size of the MFG is made smaller and more uniform. As a result, the MFGM is not able to coat the increased surface area of the MFG caused by homogenization. While some MFG lack MFGM, there is evidence that these smaller MFG get coated by the proteins, primarily casein, in milk.

While homogenization has little effect on the composition of the milk, it has important implications for the structures in the milk as well as bioactivities associated with some of these structures. Recent data suggest that the MFGM has nutraceutical properties and may represent the missing ingredient in artificial baby's milk compared to breast feeding. Suffice it to say that the MFG have evolved to provide advantages to the mammalian host for absorbing fats and producing other favorable biological outcomes.

It is believed that the MFG+/−MFGM enters the small intestine where it is complexed with bile salts, degraded and absorbed by the enterocytes lining the intestinal villi. Inside the enterocyte, the fats from the MFG+/−MFGM are assembled into chylomicrons (CM) and secreted into the lacteals, which are the lymphatic vessels inside the intestinal villi. The CM are transported to the thoracic duct then to the subclavian vein from where the CM enter into the arterial system. As a result, the CM bypass the liver and are circulated throughout the body before entering the venous system and eventually the liver.

The present invention takes advantage of this unique mode of fat transport by adding the various oils from cannabis or hemp to these MFG+/−MFGM. In various embodiments of the present invention, these MFG+/−MFGM can be obtained from milk, half-and-half, whipped cream, heavy cream, or powdered forms of these sources. Alternatively, similar fat globules can be used that are made from long chain triacylglycerols, an emulsifier such as lecithin, and proteins, such as casein, soy, or whey. The objective of the designed and/or synthesized fat globules would be to direct them to the lymphatic system before entering the circulatory system thereby improving their bioavailability.

The principal group of milk proteins, the caseins, are not soluble in water and exist in milk as smaller particles (<300 nm) called micelles. Some of these particles are likely adsorbed to the oil water interface of the MFG as previously stated.

Herein, the MFG+/−MFGM is defined as any fat globule designated to be taken up by the enterocytes and become part of the CM.

Lipophilic molecules of interest can be added to these diverse MFG+/−MFGM structures in such a manner that the lipophilic molecules enter the lipid core of the globules. The MFG+/−MFGM can be used before or after homogenization and molecules of interest can be added before, during, or after homogenization.

Hemp oil can be added to whole milk or a milk product and treated in a food processor, mixer, blender, sonicator, sonifier, homogenizer, centrifuge, stirrer, magnetic stirrer, or the like. A homogeneous mixture can result with no sign of the oil coalescing on the surface of the mixture. Fat globules from mammalian, plant, or synthetic sources can be used as exemplary sources of the MFG. Molecules of interest can be added to raw milk containing a diverse set of MFG. Molecules of interest can be added to homogenized milk containing a more uniform set of MFG. Molecules of interest can be added to homogenized or unhomogenized milk cream containing diverse sets of MFG.

In some embodiments, cream can be used as a starting point. The best ratio of cannabinoids/hemp oil to the volume of cream can be determined based on consistency, homogeneity, and stability. The amount of free cannabinoids/hemp oil remaining after mixing with cream can be measured to derive appropriate ratios of components to achieve good consistency. The taste qualities of the cannabinoids/oil globules (COG) can be ascertained and adjusted, for example, by adding sweeteners. A powder can be created by drying/evaporating the milk or cream. The powder can then be resuspended to form a solution, mixture, suspension, dispersion, emulsion, or other composition, and the stability of the composition can be evaluated.

According to various embodiments of the present invention, milk fat globules can be isolated from raw milk and mixed with hemp oil to form a mixture. The mixture can then be dried or evaporated to make a powder. The powder can then be resuspended in water, milk, or an aqueous system to make a solution, mixture, suspension, dispersion, emulsion, or other composition, and the stability of the composition can be evaluated.

According to various embodiments of the present invention, milk fat globules can be isolated from homogenized cream and mixed with hemp oil to form a mixture. The mixture can then be dried or evaporated to make a powder. The powder can then be resuspended in water, milk, or an aqueous system to make a solution, mixture, suspension, dispersion, emulsion, or other composition. According to various embodiments, homogenization can be used to improve the quality of the product.

According to various embodiments, dried MFG from any source can be used for uniform distribution and/or dosing into various forms such as water-soluble cannabinoids for food and beverage services and/or products, pill and capsule forms, forms for vaporization, forms for use within the pharmaceutical industry, combinations thereof, and the like.

The milk fat globules can come from milk or a milk product having, for example, 1% by weight milk fat or more. Low-fat milk having, for example, 2% by weight milk fat can be used. Whole milk having, for example, 4% by weight milk fat can be used. Half-and-half having, for example, about 12% by weight milk fat can be used. Light cream having, for example, 20% by weight milk fat can be used. Whipping cream having, for example, 35% by weight milk fat can be used. Heavy cream having, for example, 38% by weight milk fat can be used. Heavy cream powder having, for example, 66% by weight milk fat can be used as-is or can be reconstituted with water. The source of milk fat globules can contain, for example, from 1% by weight milk fat to 100% by weight milk fat, for example, from 2% by weight milk fat to 70% by weight milk fat, from 4% by weight milk fat to 50% by weight milk fat, from 10% by weight milk fat to 40% by weight milk fat, or from 12% by weight milk fat to 38% by weight milk fat.

EXAMPLES

Example 1

A tincture of full spectrum hemp oil was mixed with whipped cream as a source of MFG+/−MFGM. The addition of hemp oil to whipped cream initially resulted in the oil floating on the surface of the cream. This mixture was treated with a VITAMIX® blender available from Vita-Mix Management Corporation of Olmstead, Ohio. The separated oil disappeared and a homogeneous mixture remained. This homogeneous mixture was added to the refrigerator and remained stable, i.e., the oil did not coalesce on the surface of the homogeneous mixture, and there was no phase separation for at least two days.

Example 2

A tincture of full spectrum hemp oil was mixed with a milk cream as a source of MFG+/−MFGM. Several milliliters of full spectrum hemp oil were added to about 50 ml of milk cream (20% milk fat). The oil floated on the surface of the cream. The mixture was mixed with a VITAMIX® blender and the separated layer of oil disappeared. The resulting milk cream mixture was placed in a refrigerator and remained as a stable homogeneous mixture for at least a day. The homogeneous cream mixture was then placed at room temperature where it remained stable for two days.

Example 3

50 ml of hemp oil and 50 ml of milk cream were combined and mixed in a VITAMIX® blender. The result was that the cream/oil mixture became a homogeneous mixture that solidified and had a consistency of butter.

Example 4

Approximately 20 ml of hemp oil was added to about 60 ml of whole milk (4% milk fat) and treated in a VITAMIX® blender. The result was a homogeneous mixture with no sign of the oil coalescing on the surface of the mixture.

Example 5

A 10 ml aliquot of full spectrum hemp oil was added to 10 ml of commercially purchased Half and Half (HH) (12% milk fat) and 10 ml of deionized water in a 50 ml NALGENE® tube available from Nalge Nunc International Corporation, Rochester, N.Y. The mixture was not miscible, and the different phases of oil, water, and HH could be seen. A schematic view of the tube, the three layers, and the result from sonicating the tube are illustrated in FIG. 1. FIG. 1 shows a NALGENE® tube 302 capped with a cap 304 and having therein a top layer of hemp oil 306, a middle layer of deionized water 308, and a bottom layer of Half-and-Half 310. After sonication, depicted by the arrow, the three layers formed an emulsion 312. The scale of the micelles in the emulsion is exaggerated for the sake of clarity.

The less dense water settled on the surface of the half-and-half. The hemp oil, being less dense than water, settled on the surface of the water. The tube was closed and sonicated. Subsequent to sonication, an emulsion resulted having hemp oil droplets encompassed by milk fat globules, distributed in an aqueous/milk phase. Immediately following sonication, the resulting emulsion exhibited no indication of phase separation. The encompassed hemp oil droplets were suspended in the aqueous/milk phase. Then, after three weeks of storage in a refrigerator at 4° C., there were no signs of phase separation. The oil was absorbed by the milk fat globules-and-milk fat globule milk (MFG/MFGM).

As a point of reference, 10 ml each of hemp oil and water were placed in a different 50 ml NALGENE® tube. Each mixture was placed on ice and was sonicated in a Branson Model 450 sonifier (available from Emerson Electric Co., St. Louis, Mo.) using 20% of maximum amplitude for four minutes. As expected, for the control of oil and water alone, the oil began to coalesce and rose to the surface of the water soon after sonication.

With the sample including Half and Half, the oil did not separate or rise to the surface. It appears that the oil was absorbed into the lipophilic core of the MFG+/−MFGM. After three weeks at 4° C., there was no separation of the different phases. The sample was then left for six weeks in the refrigerator, and the contents of the tube looked essentially similar, thus showing that a stable emulsion had been formed.

Example 6

Figure 2:
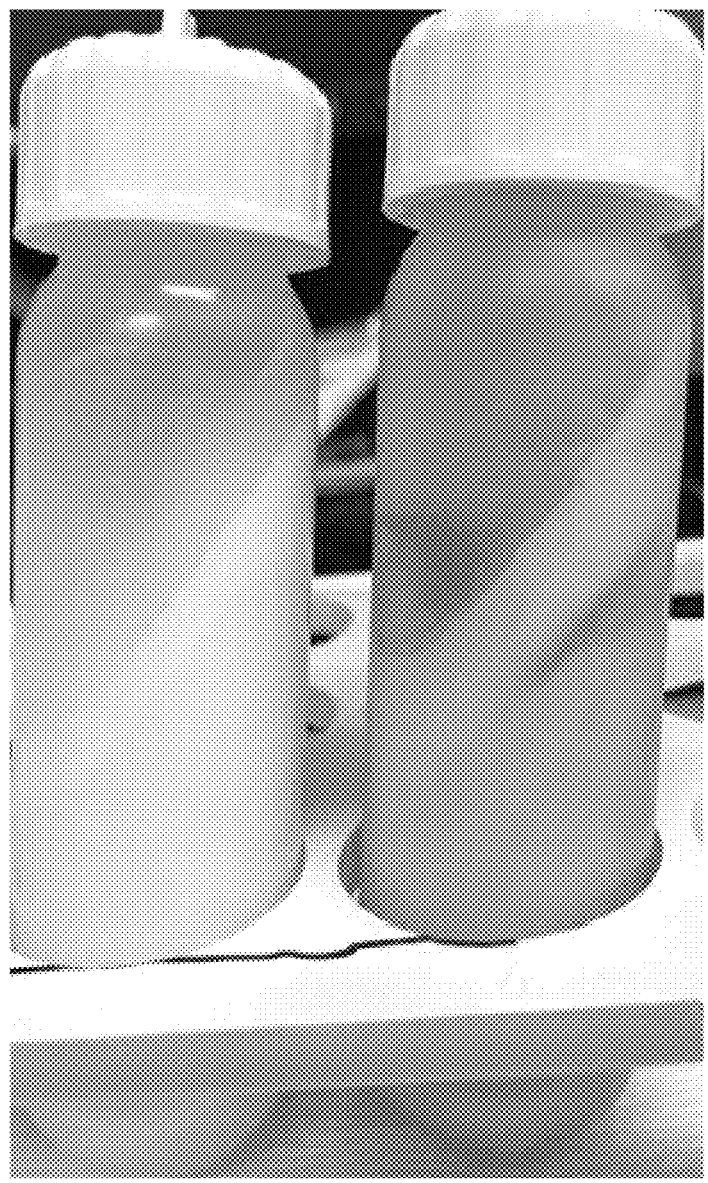
FIG. 2 is a side-by-side photograph comparing a centrifuged sample of emulsions of heavy cream (HC) with and without hemp oil, wherein the sample on the left is HC alone, and the sample on the right is HC with a 5 gram aliquot of hemp oil.

Premium Heavy Cream Powder (HC) was purchased from Hoosier Hill Farms of Fort Wayne, Ind. This material contained 66% fat such that 5 grams of powder contained 3.3 grams of fat. The material was homogenized prior to drying. The manufacturer recommends suspending 5 grams of powder in about 25 ml of water. A solution of 15 grams of HC in 75 ml of deionized water was prepared. The mixture was stirred with a magnetic stirrer until the HC was suspended in the water. A 5 gram aliquot of concentrated hemp oil extract (approximately 70% cannabidiol) was added to the HC suspension and subjected to sonication. The sample was placed in ice and was sonicated at 40% maximum amplitude for four minutes with a Branson Model 450 sonifier. The initial solution, which contained the oil floating on the surface of the aqueous HC solution, was rendered completely homogenous with the oil being miscible similar to what was observed with the HH mixture. The only difference was that on standing at 4° C. overnight, there was some separation of the liquid, but it was identical to that seen in sonicated samples of HC without the hemp oil, as shown in FIG. 2.

Samples of HC with and without hemp oil were subjected to centrifugation in a Sorvall centrifuge (available from Thermo Fisher Scientific Inc. of Waltham, Mass.) using rotor F41 spun at 10,000 rpm for ten minutes. Each sample contained three layers as shown in FIG. 2. The sample on the left is HC alone, and the sample on the right is HC with a 5-gram aliquot of hemp oil. Three layers are visible in each sample, including a top lipid layer over a liquid middle layer with a bottom pellet. Although the top layer of the HC alone sample (shown to the left in FIG. 2) is practically transparent, it can still be seen. The middle layer of the HC alone sample (shown to the left in FIG. 2) is thin and has a thickness of about the same dimension as the thickness of the top layer. The majority of the centrifuged HC alone sample (shown to the left in FIG. 2) makes up the bottom layer. Similarly, the top layer of the HC and hemp oil sample (shown to the right in FIG. 2) is practically transparent but can still be seen. The middle layer of the HC and hemp oil sample (shown to the right in FIG. 2) is thin and has a thickness of about the same dimension as the thickness of the top layer. The majority of the centrifuged HC and hemp oil sample (shown to the right in FIG. 2) makes up the bottom layer.

A sample of each layer was taken from the centrifuged HC and hemp oil sample and assayed for hemp oil cannabinoids. All three layers contained hemp oil. The layers were also examined microscopically. These results are shown for the HC and hemp oil sample, in FIGS. 3-5. The bottom layer contained large globules, the middle and upper layers contained smaller globules. Each layer was examined by HPLC to determine if the hemp oil was equally distributed among the varying sized MFG/MFGM. These results were compared to standards, as described with respect to FIG. 6 and FIG. 7.

Figure 6:
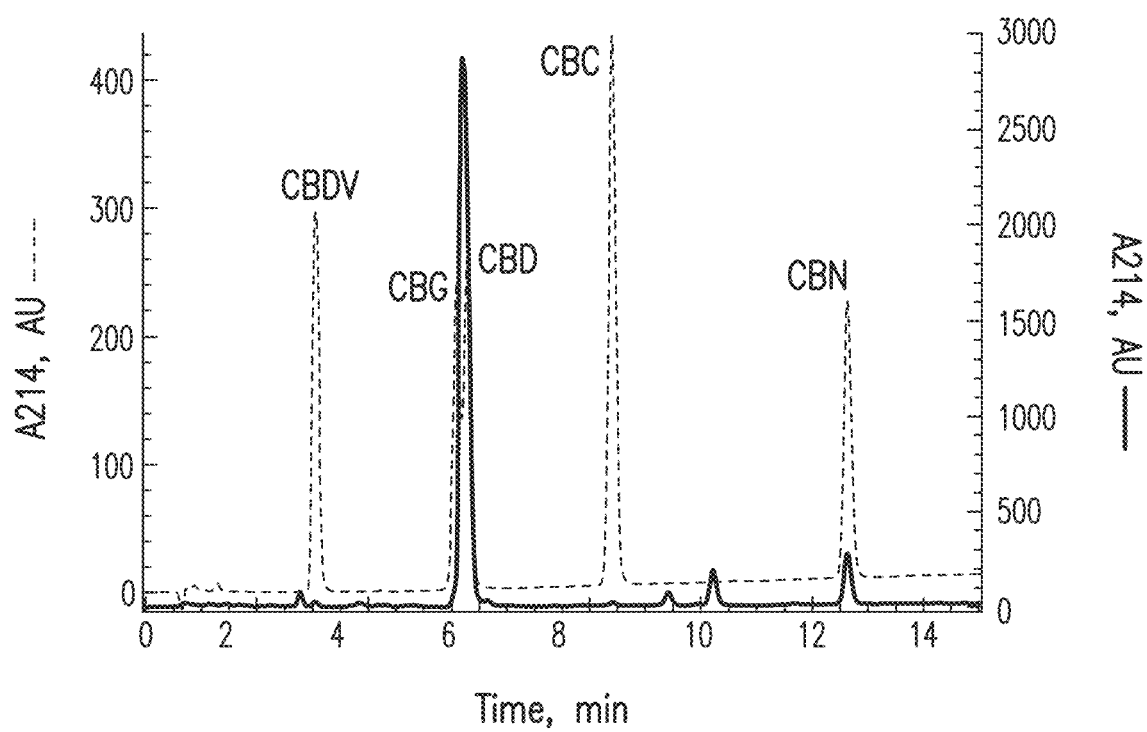
FIG. 6 is a high-performance liquid chromatographic chromatogram of hemp oil overlaying a chromatogram of cannabinoid standards.

FIG. 6 shows a high-performance liquid chromatographic chromatogram of hemp oil overlaid on a chromatogram of cannabinoid standards. As can be seen, CBG and CBD do not completely resolve. The hemp oil has small amounts of CBDV and CBC. There is a higher concentration of CBN and the bulk of the material is the CBD peak. The absence of a pre-eluting shoulder on the CBD peak suggests that the level of CBG is very small if present at all.

Figure 3:
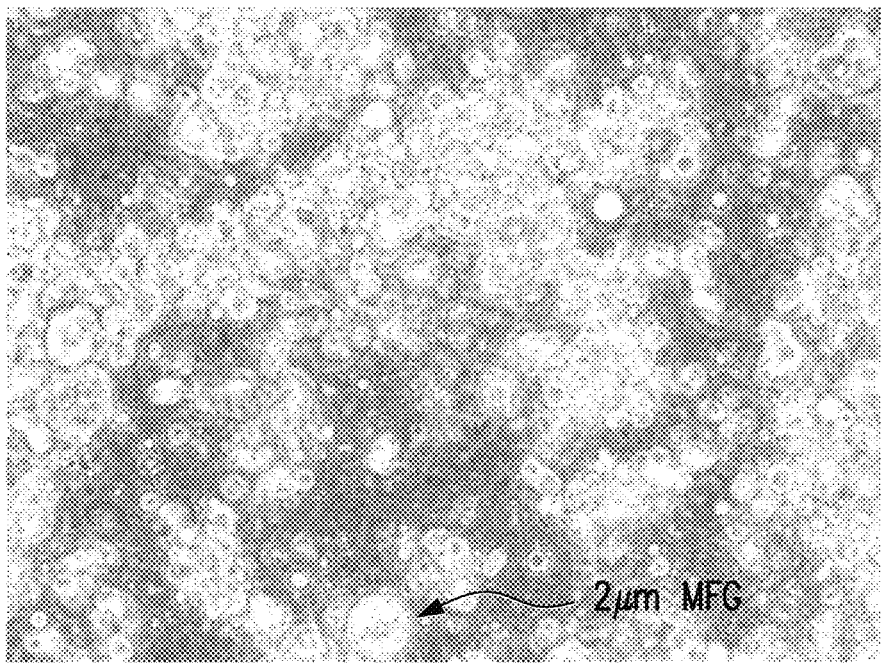
FIG. 3. is a close-up photograph of a portion of the bottom pellet shown in the centrifuged heavy cream with hemp oil emulsion shown on the right side of FIG. 2, examined with a Nikon microscope at 400× (10× eyepiece and 40× objective), wherein the large milk fat globule (MFG) at the bottom of the photograph measures approximately 2 microns in diameter.
Figure 4:
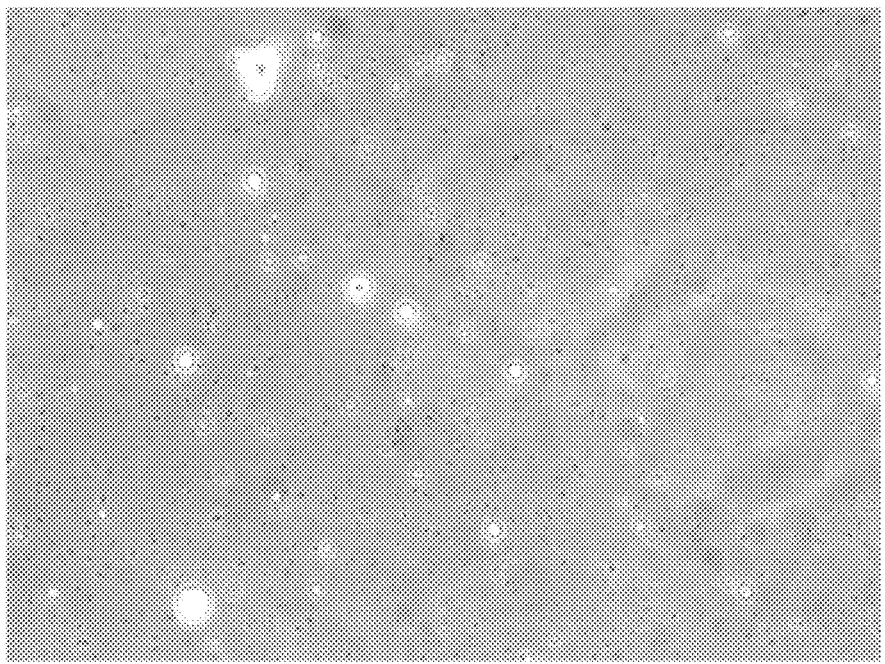
FIG. 4 is a microphotograph of the middle liquid layer of the centrifuged heavy cream with hemp oil emulsion shown on the right side of FIG. 2, examined with a Nikon microscope at 400× (10× eyepiece and 40× objective).
Figure 5:
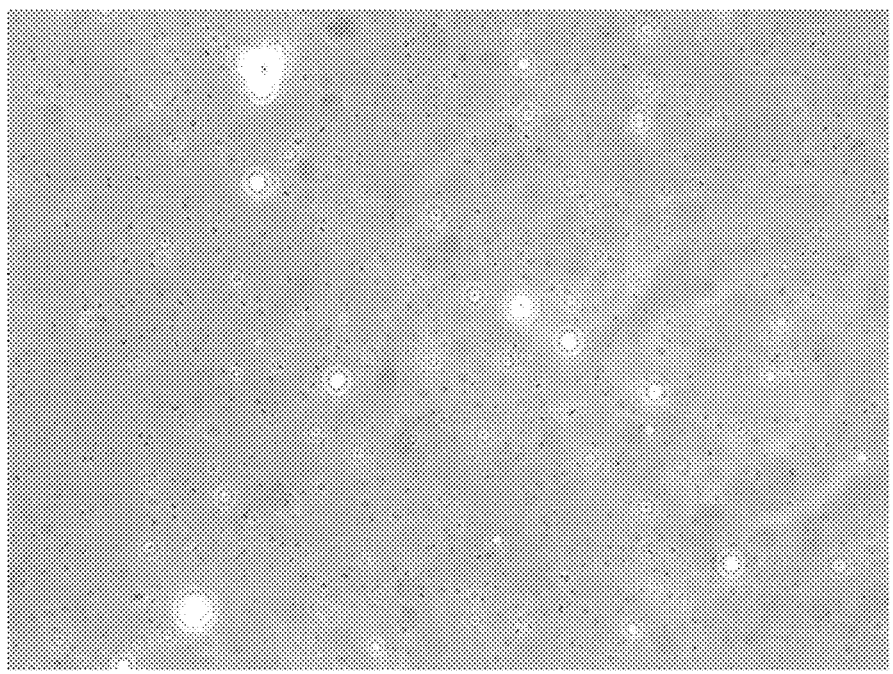
FIG. 5 is a microphotograph of the top liquid layer of the centrifuged heavy cream with hemp oil emulsion shown on the right side of FIG. 2, examined with a Nikon microscope at 400× (10× eyepiece and 40× objective).
Figure 7:
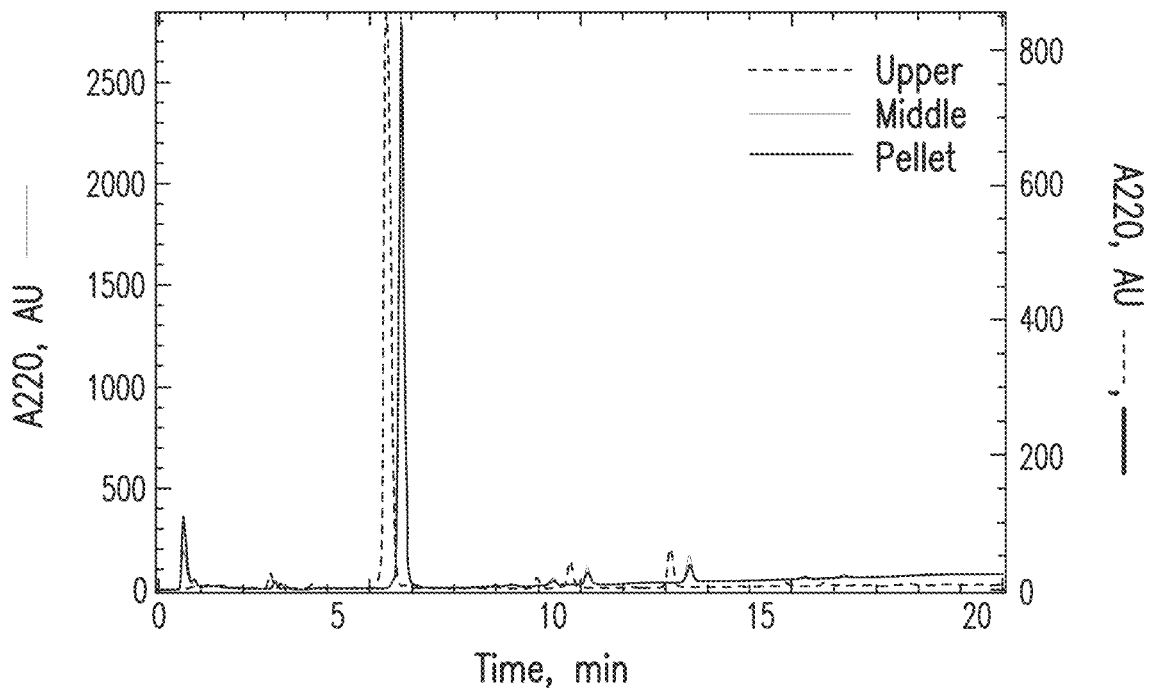
FIG. 7 is a high-performance liquid chromatographic chromatogram overlay showing overlaid chromatograms of the samples from the upper layer, the middle layer, and the bottom layer of the heavy cream with hemp oil sample shown in FIG. 2 and indicating that all three layers contain the same or a similar distribution of hemp oil.

High-performance liquid chromatographic chromatograms were then taken from the upper layer, middle layer, and bottom layer of the Heavy Cream (HC)-with-hemp oil sample shown in FIGS. 3-5 and overlaid on one another as shown in FIG. 7. As can be seen, all three layers contain the same distribution of hemp oil. In the chromatogram of the upper layer, the elution profile suggests that these components eluted about 30 seconds prior to the peaks seen in the middle and lower levels.

It is clear that each group of MFG/MFGM contains all of the components of the hemp oil. The oil is predominantly CBD as expected with the second most abundant component being CBN.

Example 7

In this experiment, 7.11 grams of hemp oil containing 70% CBD was weighed out. A 7.2 gram sample of Premium Heavy Cream Powder (HC) was added to the oil and mixed to create an approximately 1:1 ratio of HC to hemp oil. The mixture had the consistency of peanut butter. An additional quantity of HC was added to get a ratio of approximately 2:1 HC to hemp oil. This material could be readily resuspended in water although with time larger MFG+/−MFGM sediment settled out. When the settled sample was shaken, the globules resuspended easily. There was no phase separation of oil from the MFG+/−MFGM and the hemp oil micelles were soluble in water. It was then determined that there was a pH effect on the integrity of the emulsion. When the powder was suspended in deionized water the pH was about 7.5. With standing, there appeared to be aggregates that formed and attached to the side of the tube. Although these aggregates could be resuspended by shaking, dropping the pH to the 4-5 range prevented their formation. It was concluded that water emulsions can be used more quickly and not necessarily stored for more than 2 days, although longer term storage can be used. If longer storage is desired, then the powder can preferably be suspended in a slightly acidic solution such as orange juice, lemonade, vitamin water, or any other ingestible solution that has an acidic pH.

The present invention includes the following numbered aspects, embodiments, and features, in any order and/or in any combination:

1. A soluble form of a cannabinoid, hemp oil, cannabis oil, or a combination thereof, comprising, in combination, (a) a cannabinoid, hemp oil, cannabis oil or combination thereof, and (b) fat globules from a mammalian source, animal source, plant source, synthetic source, or a combination thereof, wherein components (a) and (b) have been mixed together to form a mixture, solution, emulsion, suspension, powder, paste, or other composition providing a soluble form of a cannabinoid, hemp oil, or a combination thereof.
2. The soluble form of a cannabinoid, hemp oil, cannabis oil, or a combination thereof, of any preceding embodiment/feature/aspect, wherein the source of fat globules comprises raw milk or a processed product of raw milk.
3. The soluble form of a cannabinoid, hemp oil, cannabis oil, or a combination thereof, of any preceding embodiment/feature/aspect, wherein the source of fat globules comprises a plant.
4. The soluble form of a cannabinoid, hemp oil, cannabis oil, or a combination thereof, of any preceding embodiment/feature/aspect, wherein the source of fat globules comprises a chemically synthesized source.
5. The soluble form of a cannabinoid, hemp oil, cannabis oil, or a combination thereof, of any preceding embodiment/feature/aspect, wherein the source of fat globules comprises an animal other than a mammal.
6. The soluble form of a cannabinoid, hemp oil, cannabis oil, or a combination thereof, of any preceding embodiment/feature/aspect, wherein the cannabinoid, hemp oil, cannabis oil, or combination thereof, comprises naturally occurring molecules that are purified from hemp, cannabis, or another plant source.
7. The soluble form of a cannabinoid, hemp oil, cannabis oil, or a combination thereof, of any preceding embodiment/feature/aspect, wherein the cannabinoid, hemp oil, cannabis oil, or combination thereof, is synthetically prepared.
8. The soluble form of a cannabinoid, hemp oil, cannabis oil, or a combination thereof, of any preceding embodiment/feature/aspect, wherein the cannabinoid, hemp oil, cannabis oil, or combination thereof, is derived from genetically engineered microorganisms grown in a controlled environment.
9. The soluble form of a cannabinoid, hemp oil, cannabis oil, or a combination thereof, of any preceding embodiment/feature/aspect, wherein the cannabinoid, hemp oil, cannabis oil, or combination thereof, is derived from a genetically engineered plant that is grown either in a field or a greenhouse.
10. The soluble form of a cannabinoid, hemp oil, cannabis oil, or a combination thereof, of any preceding embodiment/feature/aspect, wherein the cannabinoid, hemp oil, cannabis oil, or combination thereof, is derived from plant cell cultures.
11. The soluble form of a cannabinoid, hemp oil, cannabis oil, or a combination thereof, of any preceding embodiment/feature/aspect, wherein the cannabinoid, hemp oil, cannabis oil, or combination thereof, comprises hemp oils, cannabis oils and cannabinoids homogenized together.
12. A method of forming the soluble form of a cannabinoid, hemp oil, cannabis oil, or a combination thereof, wherein the method comprises mixing together components (a) and (b) to effect migration of component (a) into component (b).
13. The method of any preceding embodiment/feature/aspect, wherein the mixing comprises stirring together at a rate of from about 10 rpm to about 500 rpm.
14. The method of any preceding embodiment/feature/aspect, wherein the stirring comprises mixing components (a) and (b) together to form a mixture and subjecting the mixture to centrifugation to effect migration of component (a) into component (b).
15. The method of any preceding embodiment/feature/aspect, wherein component (b) comprises a powder and component (a) is mixed directly with the powder.
16. The method of any preceding embodiment/feature/aspect, wherein component (a) and component (b) are mixed together at a respective ratio of from 1:1 to 1:10.

The present invention can include any combination of these various features or embodiments above and/or below, as set forth in the foregoing sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such specific ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A water-soluble form of a lipophilic substance, comprising a lipophilic substance selected from the group consisting of a cannabinoid, hemp oil, cannabis oil, and a combination thereof, and a processed milk product comprising milk fat globules from a mammalian source, wherein the processed milk product comprises from 10% by weight to 100% by weight milk fat, the lipophilic substance and the processed milk product have been mixed together to form an emulsion, powder, or paste, the water-soluble form of the lipophilic substance comprises droplets of the lipophilic substance encompassed by the milk fat globules, and the milk fat globules of the processed milk product are more uniformly sized and smaller when compared with milk fat globules of the same milk product but that has not been processed.

2. The water-soluble form of a lipophilic substance, of claim 1, wherein the processed milk product comprises a homogenized product of raw milk.

3. The water-soluble form of a lipophilic substance, of claim 1, wherein the lipophilic substance has been synthetically prepared.

4. The water-soluble form of a lipophilic substance, of claim 1, wherein the lipophilic substance comprises an oil extract.

5. The water-soluble form of a lipophilic substance, of claim 1, wherein the lipophilic substance comprises cannabis oil.

6. The water-soluble form of a lipophilic substance, of claim 1, wherein the processed milk product comprises half-and-half, whipped cream, heavy cream, a powdered form of half-and-half, a powdered form of whipped cream, or a powdered form of heavy cream.

7. The water-soluble form of a lipophilic substance, of claim 1, wherein the processed milk product comprises a powdered form of half-and-half, a powdered form of whipped cream, or a powdered form of heavy cream.

8. The water-soluble form of a lipophilic substance, of claim 1, wherein the droplets of the lipophilic substance encompassed by the milk fat globules are distributed in an aqueous phase.

9. The water-soluble form of a lipophilic substance of claim 1, wherein the soluble form of the lipophilic substance comprises hemp oil droplets encompassed by the milk fat globules.

10. The water-soluble form of a lipophilic substance of claim 1, wherein the soluble form of the lipophilic substance comprises hemp oil droplets encompassed by the milk fat globules, distributed in an aqueous/milk phase.

11. The water-soluble form of a lipophilic substance of claim 1, wherein the soluble form of the lipophilic substance comprises a stable emulsion that remains stable for six weeks.

12. The water-soluble form of a lipophilic substance of claim 1, wherein the lipophilic substance comprises naturally occurring molecules that have been purified from hemp, cannabis, or another plant source.

13. The water-soluble form of a lipophilic substance of claim 1, wherein the lipophilic substance has been synthetically prepared.

14. The water-soluble form of a lipophilic substance of claim 1, wherein the lipophilic substance has been derived from genetically engineered microorganisms grown in a controlled environment.

15. The water-soluble form of a lipophilic substance of claim 1, wherein the lipophilic substance has been derived from a genetically engineered plant that is grown either in a field or in a greenhouse.

16. The water-soluble form of a lipophilic substance of claim 1, wherein the lipophilic substance has been derived from plant cell cultures.

17. The water-soluble form of a lipophilic substance of claim 1, wherein the lipophilic substance comprises hemp oil, cannabis oil, and cannabinoids homogenized together.

18. A method of forming the water-soluble form of the lipophilic substance, of claim 1, wherein the method comprises mixing together the lipophilic substance and the processed milk product to effect migration of the lipophilic substance into the processed milk product.

19. The method of claim 18, wherein the mixing together comprises stirring together the lipophilic substance and the processed milk product at a rate of from about 10 rpm to about 500 rpm.

20. The method of claim 19, wherein the stirring comprises mixing the lipophilic substance and the processed milk product together to form a mixture and subjecting the mixture to centrifugation to effect migration of the lipophilic substance into the processed milk product.

21. The method of claim 18, wherein the processed milk product comprises a powder, the powder comprises powdered half-and-half, powdered whipped cream, or powdered heavy cream, and the lipophilic substance is mixed directly with the powder.

22. The method of claim 21, wherein and the lipophilic substance and the processed milk product are mixed together at a respective ratio of from 1:1 to 1:10.

* * * * *